United States Patent [19]

Hagen et al.

[11] Patent Number: 4,804,404
[45] Date of Patent: Feb. 14, 1989

[54] 2 AND/OR 3-TRIFLUOROMETHYL-SUBSTITUTED QUINOLINE 8-CARBOXYLIC ACID DERIVATIVES AND THEIR USE FOR CONTROLLING UNDESIRABLE PLANT GROWTH

[75] Inventors: Helmut Hagen, Frankenthal; Ulrich Eichenauer, Frankfurt; Rolf-Dieter Kohler, Edingen-Neckarhausen; Peter Plath, Frankenthal; Thomas Liese-Sauer, Weinheim; Karl Eicken, Wachenheim; Bruno Wuerzer, Otterstadt; Norbert Meyer, Ladenburg, all of Fed. Rep. of Germany

[73] Assignee: BASF Aktiengesellschaft, Ludwigshafen, Fed. Rep. of Germany

[21] Appl. No.: 62,070

[22] Filed: Jun. 15, 1987

[30] Foreign Application Priority Data

Jun. 14, 1986 [DE] Fed. Rep. of Germany ....... 3620064

[51] Int. Cl.$^4$ .................... A01N 43/42; C07D 215/48
[52] U.S. Cl. ......................... 71/94; 546/168; 546/170
[58] Field of Search ..................... 546/170, 168; 71/94

[56] References Cited

U.S. PATENT DOCUMENTS 4,036,963  7/1977  Gialdi et al. .................... 546/170
4,497,651  2/1985  Hagen et al. .................... 546/169
4,715,889  12/1987  Hagen et al. .................... 71/94

Primary Examiner—David B. Springer
Attorney, Agent, or Firm—Keil & Weinkauf

[57] ABSTRACT

Fluoroalkyl-substituted quinoline derivatives of the formula

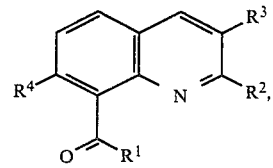

where $R^1$ is chlorine, fluorine, hydroxyl, $O^\ominus Met^\oplus$, $C_1$–$C_4$-alkoxy or a radical of the formula

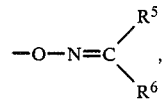

$R^2$ and $R^3$ independently of one another are each hydrogen, $C_1$–$C_3$-alkyl or $C_1$–$C_3$-fluoroalkyl, $R^4$ is fluorine, chlorine or bromine, with the proviso that one or both of the radicals $R^2$ and $R^3$ are $C_1$–$C_3$-fluoroalkyl, herbicides containing these compounds as active ingredients, and their use for controlling unwanted plant growth.

8 Claims, No Drawings

2 AND/OR 3-TRIFLUOROMETHYL-SUBSTITUTED QUINOLINE 8-CARBOXYLIC ACID DERIVATIVES AND THEIR USE FOR CONTROLLING UNDESIRABLE PLANT GROWTH

The present invention relates to novel fluoroalkyl-substituted quinoline derivatives, a process for their preparation, herbicides which contain these compounds as active ingredients, and a method for controlling undesirable plant growth.

Herbicidal quinoline-8-carboxylic acids, for example 3-haloalkyl-7-halo(5,7-dihalo)-quinoline-8-carboxylic acids, are disclosed in EP-A-O No. 104 389. However, only 3-bromomethyl-7-chloro(5,7-dichloro)-quinoline-8-carboxylic acid and its alkyl esters have been described as typical members of this class of compounds.

We have found that fluoroalkyl-substituted quinoline derivatives of the formula I

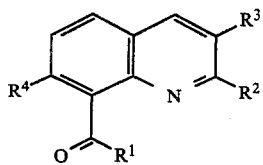

(I)

where
$R^1$ is chlorine, fluorine, hydroxyl, $O^\ominus Met^\oplus$, $C_1$–$C_4$-alkoxy or a radical of the formula

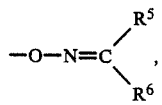

$R^2$ and $R^3$ independently of one another are each hydrogen, $C_1$–$C_3$-alkyl or $C_1$–$C_3$-fluoroalkyl,
$R^4$ is fluorine, chlorine or bromine,
$Met^\oplus$ is an alkali metal ion and
$R^5$ and $R^6$ independently of one another are each $C_1$–$C_3$-alkyl,
with the proviso that one or both of the radicals $R^2$ and $R^3$ are $C_1$–$C_3$-fluoroalkyl, have a more powerful herbicidal action and are more selective with respect to important crops than the 3-bromomethyl quinoline derivatives disclosed in EP-A-O No. 104 389.

In formula I, $R^1$ is chlorine, fluorine, hydroxyl or, for example, $O^\ominus Na^\oplus$, $O^\ominus K^\oplus$, methoxy, ethoxy, n-propoxy, isopropoxy, n-butoxy or a radical of the formula

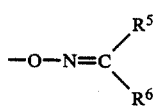

where $R^5$ and $R^6$ independently of one another are each methyl, ethyl or n-propyl. $R^1$ is preferably hydroxyl or a radical of the formula

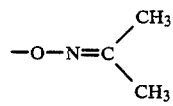

In formula I, $R^2$ and $R^3$ are each, for example, hydrogen, methyl, ethyl, n-propyl, isopropyl or $C_1$–$C_3$-fluoroalkyl, such as fluoromethyl, difluoromethyl, trifluoromethyl, 1-fluoroethyl, 1,1-difluoroethyl, 2,2-difluoroethyl, 2,2,2-trifluoroethyl, 3,3,3-trifluoro-n-propyl or pentafluoroethyl, one or both of the radicals $R^2$ and $R^3$ being fluoroalkyl. A preferred fluoroalkyl radical is trifluoromethyl.

In formula I, $R^4$ is fluorine, chlorine or bromine, preferably chlorine.

The quinoline derivatives of the formula I are obtained by reacting a compound of the formula II

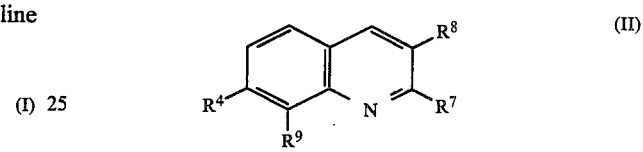

(II)

where
$R^4$ has the above meanings,
$R^9$ is methyl or carboxyl and one or both of the substituents
$R^7$ and $R^8$ are formyl, acetyl, carboxyl, carboxymethyl, carboxyethyl or formylmethyl and, where relevant, the other substituent is hydrogen or $C_1$–$C_3$-alkyl, with sulfur tetrafluoride, subsequent oxidation to carboxyl being effected where $R^9$ is methyl.

The reaction with sulfur tetrafluoride, by means of which the structure C—OH is converted to C—F and C=O to CF$_2$, is carried out in the presence of an inert diluent, for example a halohydrocarbon such as methylene chloride, chloroform, carbon tetrachloride, dichloroethane, trichloroethane, hexachloroethane or trifluorotrichloroethane, or an aromatic, such as benzene, chlorobenzene or toluene, and in the presence of from 0 to 100 equivalents of hydrofluoric acid, using from 1 to 20 equivalents of sulfur tetrafluoride, under superatmospheric pressure and at elevated temperatures. Chlorohydrocarbons and 10–50 equivalents of hydrofluoric acid are preferred as the reaction medium, while the reaction temperature is preferably 80°–160° C. The oxidation of methyl to carboxyl can be carried out in one or more stages. A preferred procedure comprises bromination of the methyl group and subsequent oxidation.

For this purpose, the compound possessing the methyl group in the 8-position is reacted with the halogenating agent, such as bromine, chlorine, N-bromosuccinimide, N-chlorosuccinimide, N-chloroacetamide, N-bromoacetamide, N-chlorophthalimide or N-bromophthalimide, in the presence of an inert diluent at elevated temperatures, the typical conditions of a free radical reaction (presence of a free radical initiator, exposure to light) being advantageous but not absolutely essential.

Suitable inert diluents are perhalogenated hydrocarbons, such as tetrachloromethane, hexachloroethane or trifluorotrichloroethane, or chlorinated aromatics, such as chlorobenzene or dichlorobenzene. The reaction temperature chosen can be from 60° to 180° C., depending on the diluent; suitable free radical initiators are azo compounds, such as azobisisobutyronitrile, and peroxides, such as dibenzoyl peroxide. Diffuse sunlight is sufficient for exposure, although this may be reinforced by lamps.

Preferred reaction conditions comprise chlorobenzene as the reaction medium, temperatures of from 80° to 120° C., particularly preferably from 90° to 110° C., and azobisisobutyronitrile as the free radical initiator.

The oxidation of the 8-bromomethylquinolines to quinoline-8-carboxylic acids is carried out in a conventional manner by reaction with nitric acid in sulfuric acid or in a carboxylic acid, such as propionic acid, advantageously at from 100° to 140° C.

2-Trifluoromethylquinoline-8-carboxylic acids can be obtained by reacting a 2-trifluoromethyl-3,1-benzoxazin-4-one with an enamine by the process described in Angew. Chem. 85 (1973), 505. For this purpose, the substituted 2-trifluoromethyl-3,1-benzoxazinone of the formula III

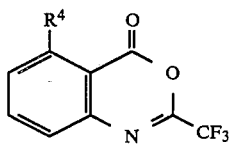
(III)

where $R^4$ has the above meanings, obtained from the corresponding anthranilic acid by cyclization with trifluoroacetic anhydride, is reacted with an enamine of the formula (IV)

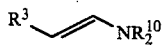
(IV)

where $R^3$ is $C_1$–$C_3$-alkyl and $NR_2^{10}$ is di-($C_1$–$C_3$-alkyl)-amino, in a polar aprotic solvent, such as acetonitrile, dimethylformamide, N-methylpyrrolidone or tetrahydrofuran, at from $-10°$ to $+50°$ C. Acetonitrile is a preferred solvent, and temperatures of from 0° to 30° C. are preferred.

The Examples which follow illustrate the invention without restricting it.

EXAMPLE 1

3-trifluoromethyl-7-chloroquinoline-8-carboxylic acid (No. 1 in Table 1)

(1a) 120 g of hydrofluoric acid and 140 g of sulfur tetrafluoride are added to a solution of 58 g (0.23 mole) of 7-chloroquinoline-3,8-dicarboxylic acid in 200 ml of methylene chloride in a stirred Hasteloy C autoclave having a capacity of 1.2 l, and the mixture is stirred for 10 hours at 120° C. After the mixture has cooled, the volatile components are stripped off in a rotary evaporator. The residue is poured onto ice and extracted with methylene chloride. An insoluble solid is separated off by filtration and discarded. The methylene chloride phase is dried over magnesium sulfate, after which the solvent is evaporated off and the resulting residue is recrystallized from n-hexane. 27 g (42%) of 3-trifluoromethyl-7-chloroquinoline-8-carbonyl fluoride of melting point 98°–99° C. are obtained.

(1b) 10 g (36 millimoles) of the acid fluoride obtained under (a) are combined with 70 ml of 5% strength sodium hydroxide solution, and the mixture is stirred for 5 minutes at 100° C. Insoluble components are filtered off, and the filtrate is then acidified with concentrated hydrochloric acid (pH 3). The precipitated solid is isolated by filtration under suction, washed with water and dried at 50° C. under reduced pressure to give 7.4 g (75%) of 3-trifluoromethyl-7-chloroquinoline-8-carboxylic acid of melting point 250° C.

EXAMPLE 2

Acetone oxime ester of 3-trifluoromethyl-7-chloroquinoline-8-carboxylic acid (No. 2 in Table 1).

3.65 g (50 millimoles) of acetone oxime and 7.9 g (0.1 mole) of pyridine are added to a solution of 16.7 g (50 millimoles) of the acid fluoride obtained under (1a) in 100 ml of 1,1,1-trichloroethane, and the mixture is then stirred for 3 hours at 70° C. After the mixture has been cooled, it is extracted with 5% strength hydrochloric acid neutralized with sodium bicarbonate solution, dried over magnesium sulfate and evaporated down. The remaining oily residue becomes crystalline on trituration with diethyl ether. Melting point: 105°–107° C.; yield: 8.5 g (51%).

EXAMPLE 3

2-trifluoromethyl-3-ethyl-7-chloroquinoline-8-carboxylic acid (No. 3 in Table 1)

(a) 5-chloro-2-trifluoromethyl-3,1-benzoxazin-4-one 6-chloroanthranilic acid is acetylated with trifluoroacetic anhydride, and the product is cyclized with boiling acetic anhydride.

Melting point: 91°–93° C.; yield 86%.

(b) A solution of 5.1 g (40 millimoles) of 1-diethylamino-but-1-ene in 10 ml of acetonitrile is added dropwise, at 0° C., to a solution of 10.0 g (40 millimoles) of 5-chloro-2-trifluoromethyl-3,1-benzoxazin-4-one in 50 ml of dry acetonitrile. The mixture is stirred for 16 hours at room temperature, after which the precipitated solid is isolated by filtration under suction, washed with diethyl ether and suspended in 30 ml of water. 12 ml of 2N NaOH are added, after which the mixture is filtered and the filtrate is acidified to pH 3 with 2N hydrochloric acid. The precipitated solid is isolated, washed with water and dried at 60° C. under reduced pressure.

Yield: 4.6 g (38%); melting point: 178°–180° C.

EXAMPLE 4

2-trifluoromethyl-3-methyl-7-chloroquinoline-8-carboxylic acid (No. 4 in Table 1)

2-trifluoromethyl-3-methyl-7-chloroquinoline-8-carboxylic acid of melting point 186°–188° C. is prepared, in a yield of 41%, from 5-chloro-2-trifluoromethyl-3,1-benzoxazin-4-one and 1-diethylaminoprop-1-ene, using a method similar to that described in Example 3.

EXAMPLE 5

2,3-bis-(trifluoromethyl)-7-chloroquinoline-8-carboxylic acid (No. 5 in Table 1)

(a) 2,3-bis-(trifluoromethyl)-7-chloro-8-methylquinoline 50 g of 7-chloro-8-methylquinoline-2,3-dicarboxylic acid, 120 ml of methylene chloride, 45 g of hydrofluoric acid and 190 g of sulfur tetrafluoride are heated at 120° C. for 10 hours in a stirred Hasteloy C autoclave having a capacity of 0.5 l. After cooling, the mixture is poured into ice water and extracted by shaking with methylene chloride, the organic phase is dried and the solvent is then removed in a rotary evaporator. The crude product is purified by adsorptive filtration with pentane over silica gel; 34.8 g (58%) of 2,3-bis-(trifluoromethyl)-7-chloro-8-methylquinoline of melting point 70°-73° C. are isolated.

(b) 2,3-bis-(trifluoromethyl)-8-bromomethyl-7-chloroquinoline 3.1 g of the compound from (a) are refluxed for 3 hours with 4.45 g of N-bromosuccinimide and 0.2 g of azobisisobutyronitrile in 30 ml of chlorobenzene. The solvent is removed in a rotary evaporator, dimethylformamide is added and the mixture is poured onto water. 2.85 g (73%) of the 8-bromomethylquinoline derivative of melting point 62°-65° C. crystallize out.

(c) 2.4 g of 2,3-bis-(trifluoromethyl)-8-bromomethyl-7-chloroquinoline are suspended in 6.8 g of propionic acid and 6.8 g of 70% strength sulfuric acid, and 5.5 g of 65% strength nitric acid are added dropwise at 120° C. After 2 hours at 120° C., the mixture is diluted with water and the precipitate is filtered off under suction, washed and dried; 1.7 g (84%) of 2,3-bis-(trifluoromethyl)-7-chloroquinoline-8-carboxylic acid of melting point 108°-111° C. are isolated.

Examples of compounds I according to the invention are given in the table below.

| Nr. | $R^1$ | $R^2$ | $R^3$ | $R^4$ | mp [°C.] |
|---|---|---|---|---|---|
| 1 | OH | H | $CF_3$ | Cl | 250 |
| 2 | $O-N=C(CH_3)_2$ | H | $CF_3$ | Cl | 105–107 |
| 3 | OH | $CF_3$ | $C_2H_5$ | Cl | 178–180 |
| 4 | OH | $CF_3$ | $CH_3$ | Cl | 186–188 |
| 5 | OH | $CF_3$ | $CF_3$ | Cl | 108–111 |
| 6 | $O-N=C(CH_3)_2$ | $CF_3$ | $CF_3$ | Cl | 91 |
| 7 | $O-N=C(C_2H_5)_2$ | H | $CF_3$ | Cl | |
| 8 | $O-N=C(CH_3)C_2H_5$ | H | $CF_3$ | Cl | |
| 9 | $O-N=C(C_3H_7)_2$ | H | $CF_3$ | Cl | |
| 10 | ONa | H | $CF_3$ | Cl | |
| 11 | OH | H | $CF_3$ | F | |
| 12 | OH | H | $CF_3$ | Br | |
| 13 | $OCH_3$ | H | $CF_3$ | Cl | |
| 14 | $OC_2H_5$ | H | $CF_3$ | Cl | |
| 15 | OH | H | $CHF_2$ | Cl | |
| 16 | OH | H | $CF_2-CH_3$ | Cl | |
| 17 | OH | H | $CH_2-CF_3$ | Cl | |
| 18 | OH | $CF_3$ | H | Cl | |
| 19 | OH | $CH_2-CF_3$ | H | Cl | |
| 20 | OH | $CH_3$ | $CF_3$ | Cl | |
| 21 | OH | H | $CH_2F$ | Cl | |
| 22 | OH | H | $CH_2-CH_2-CF_3$ | Cl | |
| 23 | OH | $CF_3$ | $CH_3$ | Br | |
| 24 | OH | $CF_3$ | $C_2H_5$ | Br | 183–186 |
| 25 | OH | $CF_3$ | $CF_3$ | F | |
| 26 | OH | $CH_3$ | $CH_3$ | Cl | 200–201 |
| 27 | $OCH_3$ | H | $CH_3$ | F | 82–84 |

The fluoroalkyl-substituted quinoline derivatives of the formula I may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin and tetrahydronaphthalene, alkylated naphthalenes and their derivatives such as methanol, ethanol, propanol, butanol, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acid, phenolsulfonic acid, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 2 is mixed with 10 parts by weight of N-methyl-alpha-pyrrolidone. A mixture is obtained which is suitable for application in the form of very fine drops.

II. 20 parts by weight of compound no. 1 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 2 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 1 is dissolved in a mixture consisting of 25 parts by weight of cyclohexanol, 65 parts by weight of a mineral oil fraction having a boiling point between 210 g and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 3 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 4 is intimately mixed with 97 parts by weight of particulate kaolin. A dust is obtained containing 3% by weight of the active ingredient.

VII. 30 parts by weight of compound no. 4 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 1 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

IX. 40 parts by weight of compound no. 2 is dissolved in 60 parts by weight of a mixture consisting of 93 wt% xylene and 7 wt% of the adduct of 8 moles of ethylene oxide and 1 mole of nonylphenol. A solution is obtained containing 40 wt% of the active ingredient.

The active ingredients, or agents containing them, may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amounts of active ingredient applied depends on the time of the year, the plants to be combated and their growth stage, and varies from 0.05 to 5 kg/ha, but is preferably from 0.05 to 3 kg/ha.

The herbicidal action of compounds of the formula I is demonstrated in greenhouse experiments.

The vessels employed were plastic flowerpots having a volume of 300 cm³, and which were filled with a sandy loam containing about 3.0% humus. Peat was added to the soybean plants to ensure better growth. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rates were 0.06, 0.125, 0.25 and 0.5 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. For this treatment, either plants which had been sown directly in the pots and grown there were selected, or plants which had been grown from seedlings and were transplanted to the pots a few days before treatment. The application rates for postemergence treatment were for example 3.0 and 0.5 kg of active ingredient per hectare. No covers were placed on the vessels in this method.

The pots were set up in the greenhouse—species from warmer areas at from 20° C. to 35° C., and species from moderate climates at 10° to 20° C. The experiments were run for up to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plants used in the greenhouse experiments were *Avena sativa, Daucus carota, Galium aparine, Glycine max., Ipomoea* spp., *Triticum aestivum*, and *Zea mays*.

The agent used for comparison purposes was 3-bromomethyl-7-chloroquinoline-8-carboxylic acid (A) disclosed in EP-A-O No. 104 389.

On preemergence application, compound no. 1 is much more active in carrots as indicator plants than comparative agent A (Table 1). Carrots are extremely sensitive bioindicators for herbicidal quinolinecarboxylic acids and are suitable for biologically proving their presence (Characteristics of the new herbicide BAS 518 H, 1985 British Crop Protection Conference-Weeds 63–70). Furthermore, compound no. 1 also selectively combats, on preemergence application, unwanted broadleaved weeds, such as Ipomoea species, in soybeans (Table 2).

On postemergence application, compound no. 2 combats unwanted broadleaved plants without damaging oats (Table 3). Compound no. 1 too is, on postemergence application, more effective than comparative agent A on unwanted broadleaved plants; wheat and Indian corn for example are not damaged.

The test results are given in the following tables:

TABLE 1

| Comp. no. | Appl. rate (kg/ha) | Percentage damage to *Daucus carota* |
|---|---|---|
| 1 | 0.25 | 100 |
| A | 0.25 | 45 |

TABLE 2

| Comp. no. | Appl. rate (kg/ha) | Test plants and percentage damage | |
|---|---|---|---|
| | | Glycine max. | Ipomoea spp. |
| 1 | 0.06 | 2 | 80 |
| | 0.125 | 6 | 89 |
| | 0.25 | 8 | 95 |
| | 0.5 | 11 | 96 |

TABLE 3

| Comp. no. | Appl. rate (kg/ha) | Test plants and percentage damage | | |
|---|---|---|---|---|
| | | Avena sativa | Galium aparine | Ipomoea spp. |
| 2 | 3.0 | 0 | 90 | 100 |

TABLE 4

| Comp. no. | Appl. rate (kg/ha) | Test plants and percentage damage | | | |
|---|---|---|---|---|---|
| | | Triticum aestivum | Zea mays | Galium aparine | Ipomoea spp. |
| A | 0.5 | 0 | 10 | 60 | 20 |
| 1 | 0.5 | 0 | 0 | 90 | 80 |

In view of the spectrum of weeds that can be combated, the tolerance of the active ingredients by crop plants, and in view of the numerous application methods available, the quinoline derivatives according to the invention, or agents containing them, may be used in a large number of crops for removing unwanted plant growth. The following may be mentioned by way of example:

| Botanical name | Common name |
|---|---|
| Allium cepa | onions |
| Ananas comosus | pineapples |
| Arachis hypogaea | peanuts (groundnuts) |
| Asparagus officinalis | asparagus |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | bermudagrass |
| Daucus carota | carrots |
| Elaeis guineensis | oil palms |
| Fragaria vesca | strawberries |

| Botanical name | Common name |
| --- | --- |
| Glycine max | soybeans |
| Gossypium hirsutum (Gossypium arboreum, Gossypium herbaceum, Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactua sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the quinoline derivatives of the general formula I may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, other diphenyl ethers, triazinones, uracils, benzofuran derivatives, cyclohexane-1,3-dione derivatives, etc.

It may also be useful to apply the quinoline derivatives of the formula I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies, such as ammonium sulfate. Non-phytotoxic oils and oil concentrates may also improve the herbicidal action.

We claim:

1. A fluoroalkyl-substituted quinoline derivative of the formula

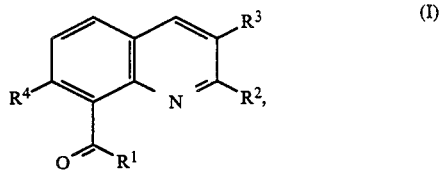

where $R^1$ is chlorine, fluorine, hydroxyl, $O^\ominus Met^\oplus$, $C_1$-$C_4$-alkoxy or a radical of the formula

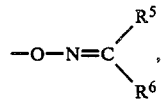

$R^2$ and $R^3$ independently of one another are each hydrogen, $C_1$-$C_3$-alkyl or $CF_3$, $R^4$ is fluorine, chlorine or bromine, $Met^\ominus$ is an alkali metal ion and $R^5$ and $R^6$ independently of one another are each $C_1$-$C_3$-alkyl, with the proviso that one or both of the radicals $R^2$ and $R^3$ are $CF_3$.

2. 3-Trifluoromethyl-7-chloro-8-carboxylic acid.

3. A herbicide containing inert additives and an effective amount of a fluoroalkyl-substituted quinoline derivative of the formula I as set forth in claim 1.

4. A process for controlling the growth of unwanted plants, wherein the unwanted plants or the area to be kept free from unwanted plant growth are treated with a herbicidally effective amount of a fluoroalkyl-substituted quinoline derivative of the formula I as set forth in claim 1.

5. A compound of the formula I as defined in claim 1, wherein $R^2$ is H and $R^3$ is $CF_3$.

6. A herbicide as defined in claim 3, wherein the active agent is 3-trifluoromethyl-7-chloro-8-carboxylic acid.

7. A process as set forth in claim 4, wherein the active agent is 3-trifluoromethyl-7-chloro-8-carboxylic acid.

8. A compound of the formula I as defined in claim 1, wherein $R^1$ is O—N=C(CH$_3$)$_2$, $R^2$ is H, $R^3$ is $CF_3$ and $R^4$ is chlorine.

* * * * *